United States Patent [19]

Cummings

[11] 4,326,924
[45] Apr. 27, 1982

[54] STABILIZATION OF METHYLCHLOROFORM

[75] Inventor: Frances M. Cummings, Corpus Christi, Tex.

[73] Assignee: PPG Industries, Inc., Pittsburgh, Pa.

[21] Appl. No.: 207,520

[22] Filed: Nov. 17, 1980

Related U.S. Application Data

[63] Continuation of Ser. No. 61,799, Jul. 30, 1979, abandoned.

[51] Int. Cl.³ ............................................. B01D 3/34
[52] U.S. Cl. ....................................... 203/6; 203/64; 570/262
[58] Field of Search .................. 203/6, 8, 9, 30, 64; 208/47; 260/652 P, 652.5 R, 652.5 P; 570/216, 238, 262

[56] References Cited

U.S. PATENT DOCUMENTS 4,065,323  12/1977  Cormany .................... 260/652.5 R

FOREIGN PATENT DOCUMENTS 49-4444  2/1974  Japan ............................ 260/652.5 R
990499   4/1965  United Kingdom .

Primary Examiner—Frank Sever
Attorney, Agent, or Firm—George D. Morris; Edward J. Whitfield

[57] ABSTRACT

Methylchloroform undergoing purification distillation is stabilized against decomposition by conducting the distillation in the presence of polyalkylene glycol having an average molecular weight greater than 150.

7 Claims, No Drawings

STABILIZATION OF METHYLCHLOROFORM

This is a continuation of application Ser. No. 61,799, filed July 30, 1979 now abandoned.

BACKGROUND OF THE INVENTION

Methylchloroform, a commonly used degreasing solvent may be prepared by liquid phase hydrochlorination of vinylidene chloride in the presence of a Friedel-Krafts catalyst, e.g., ferric chloride, as described for example in U.S. Pat. No. 2,209,000. Regardless of the mode of the preparation methylchloroform is typically recovered from the crude reaction mixture by distillation, however during distillation, methylchloroform tends to decompose to vinylidene chloride and hydrogen chloride which vinylidene chloride tends to polymerize often resulting in equipment fouling.

It is desirable therefore, to provide means for inhibiting decomposition of methylchloroform undergoing purification distillation as well as to provide means for inhibiting polymerization of methylchloroform decomposition product, i.e., vinylidene chloride.

SUMMARY OF THE INVENTION

In accordance with this invention, it has been found that in the purification distillation of methylchloroform, decomposition of the methylchloroform is inhibited by distilling the methylchloroform in the presence of a decomposition inhibiting amount of polyalkylene glycol having an average molecular weight in the range from about 300 to about 500. Polyalkylene glycol, for use as a methylchloroform decomposition inhibitor according to the invention should be highly miscible with methylchloroform, have a low vapor pressure, and a high boiling point to assure that the polyalkylene glycol will remain in solution in liquid methylchloroform and will not co-distill during purification distillation.

Polyalkylene glycol for use in accordance with the invention has a molecular weight in the range of about 300 to about 500. Polyethylene glycol and polypropylene glycol having the requisite molecular weight are preferred. Polyethylene glycol having molecular weight in the range of from about 380 to about 420 has been found to be eminently well-suited for use in the invention.

The quantity of polyalkylene glycol may vary over a considerable range, for example from about 0.01 up to about 1.0 percent or more by weight based on the weight of crude methylchloroform undergoing purification distillation may be used. It is however contemplated that the most satisfactory results will obtain in the range of from about 0.02 to about 0.1, preferably from about 0.025 to about 0.05 percent by weight polyalkylene glycol based on the weight of methylchloroform undergoing purification distillation.

The polyalkylene glycol is preferably added to the methylchloroform prior to purification distillation, however, it is also contemplated that the polyalkylene glycol be added directly to the distillation column. Alternatively a portion of the polyalkylene glycol may be added to the methylchloroform prior to its introduction to the distillation column with the remaining portion of the polyalkylene glycol being added to the distillation column.

Purification distillation of methylchloroform is conducted in known fashion using apparatus well-known to the art. For example, distillation is typically conducted at a temperature in the range of from about 130° C., to about 160° C., at a pressure in the range of from about 10 psig to about 80 psig, methylchloroform being removed as a light or overhead fraction.

The invention is further illustrated by the following Examples:

In one experiment a crude methylchloroform (MC) containing 45 weight percent methylchloroform was charged to a scale reboiler test apparatus and was tested at a temperature of about 290° F. and a pressure of about 40 psig. A second experiment was conducted under identical conditions except that the crude methylchloroform contained 0.025 weight percent (250 ppm) of polyethylene glycol (PEG) having an average molecular weight of about 400. Vinylidene chloride content of the test liquids were determined at intervals with the following results.

| | Vinylidene Chloride in Test Liquid, Wt.-Percent | |
|---|---|---|
| Time, minutes | Crude MC | Crude MC + 250 ppm PEG |
| 0 | 0 | 0 |
| 15 | 0.08 | 0 |
| 30 | 4.46 | 0.08 |
| 45 | 4.11 | 0.09 |
| 60 | 5.89 | 2.24 |
| 75 | 10.10 | 5.35 |
| 90 | — | 5.95 |
| 120 | — | 6.40 |

As can be seen from an inspection of the above data the ratio of vinylidene chloride formation in the crude methylchloroform to which no polyethylene glycol was added was quite rapid resulting in decomposition of about 43 percent of the methylchloroform to vinylidene chloride after about 75 minutes as compared with the quite gradual rate of decomposition of crude methylchloroform that had been stabilized by the addition of polyethylene glycol.

Although the invention has been in the foregoing by specific reference to and details of embodiments thereof, it is to be understood that it is not meant to be so limited since variations may be made therein by those skilled in the art that are within the intended scope of the invention as defined by the appended claims.

What is claimed is:

1. In a process for purifying crude methylchloroform by distillation wherein the improvement resides in distilling the crude methylchloroform in the presence of from about 0.02 to 0.1 percent by weight, based on weight of crude methylchloroform, of polyalkylene glycol having an average molecular weight of from about 300 to about 500 so as to inhibit the rate of decomposition of methylchloroform to vinylidene chloride and so as to not significantly co-distill with methylchloroform during said distillation.

2. The improvement of claim 1 wherein the polyalkylene glycol is polypropylene glycol or polyethylene glycol.

3. The improvement of claim 2 wherein the polyalkylene glycol is polyethylene glycol having an average molecular weight of from about 380 to about 420.

4. The improvement of claim 1 wherein polyalkylene glycol is present in an amount of from about 0.025 to about 0.05 percent by weight.

5. The improvement of claim 1 wherein the polyalkylene glycol is added to the impure methylchloroform prior to distillation.

6. The improvement of claim 1 wherein said crude methylchloroform is the crude reaction mixture formed during the preparation of methylchloroform.

7. The improvement of claim 1 wherein said distillation is conducted at a temperature in the range of from about 130° C. to about 160° C. and at a pressure in the range of from about 10 psig to about 80 psig.

* * * * *